United States Patent
Story

(10) Patent No.: US 6,712,209 B2
(45) Date of Patent: Mar. 30, 2004

(54) FLOWER SLEEVE HOLDING PRESERVATIVE

(76) Inventor: Shelby G. Story, 135 Aldenglen Dr., So. San Francisco, CA (US) 94080

( * ) Notice: Subject to any disclaimer, the term of this patent is extended or adjusted under 35 U.S.C. 154(b) by 77 days.

(21) Appl. No.: 10/100,318

(22) Filed: Mar. 13, 2002

(65) Prior Publication Data

US 2003/0173245 A1 Sep. 18, 2003

(51) Int. Cl.[7] ............................................... B65D 85/50
(52) U.S. Cl. ................... 206/423; 47/58.1 CF; 47/41.01
(58) Field of Search ................... 47/57.5, 41.1, 47/65, 72, 84, 41.13, 901, 58.1 CF; 206/423, 561, 562

(56) References Cited

U.S. PATENT DOCUMENTS 3,376,666 A * 4/1968 Leonard ..................... 206/423
6,018,908 A * 2/2000 Charrin et al. ............. 47/41.01
6,405,481 B1 * 6/2002 Bautner ......................... 47/77

* cited by examiner

*Primary Examiner*—Shian Luong
(74) *Attorney, Agent, or Firm*—Robert Samuel Smith

(57) ABSTRACT

A flower sleeve, being a package for a bouquet of flowers, comprising a tube of a plastic film, open at a large end and sealed at an opposite smaller end. An opening is formed near the smaller end of the tube. One edge of a flap is adhered on an inside surface of the tube that closes off the opening when pressure is applied to the flap from inside the tube. A panel adhered to the outside of the tube forms a pocket over the opening. A pocket opening permits inserting the nozzle of a wand into the pocket to inject preservative gel through the opening into the region of the tube adjacent to the sealed end of the tube. Once the gel is injected into the tube, the flap on the inside of the tube functions like a oneway valve to prevent escape of the gel out of the tube through the opening.

17 Claims, 2 Drawing Sheets

1. PROVIDE TUBE OF FLEXIBLE SHEET

2. FORM SECOND OPENING WITH FLAP INSIDE THE TUBE

3. SEAL ONE END OF THE TUBE

4. FORM A POCKET OVER THE SECOND OPENING WITH FLAP

FIG. 1

1. PLACE BOUQUET IN SLEEVE

2. INSERT NOZZLE OF WAND INTO POCKET

3. SQUIRT GEL THROUGH POCKET INTO TUBE 4. (OPTIONAL) WRAP RUBBER BAND AROUND STEMS

FIG. 6

FLOWER SLEEVE HOLDING PRESERVATIVE

FIELD OF THE INVENTION

This invention relates to flower sleeves used to package cut flowers and particularly to a flower sleeve that holds a preservative for preserving flowers.

BACKGROUND AND INFORMATION DISCLOSURE

The customary package for transporting a bunch of flowers is the so-called "flower sleeve".

The flower sleeve is a tube of thin plastic sheet, usually transparent cellophane and typically 0.005 inches thick. Oftentimes, one end of the tube is larger than the opposite end to accommodate the blossoms on one end of the bunch.

The present day market for cut flowers requires that many orders be shipped over long distances taking periods of several days. The condition of flowers subject to this procedure deteriorates in direct proportion to the length of time. A primary reason for the deterioration is that, the cut flower is deprived of normal "nutrients", i.e., minerals and fertilizers as well as water that are absorbed by the uncut flower in its growing state. In cut condition, the flower "cannibalizes", i.e., the flower transfers essential nutrients from certain parts (the lower part of the stem) to regions such as the blossoms in an effort to sustain normal function. The stems, adjacent to the roots, are the first part of the flower to show the deteriorating process that is taking place.

In order to prolong the freshness of the flower, nutrients in the form of gels have been developed. The advantage of surrounding the cut ends of the stems in such compositions is that the gel is obviously more secured in location adjacent the stem than is a liquid (water). However, it is difficult to dispense the gel through out the base of the stems of a bunch of flowers when the base of stems is confined in the flower sleeve that is presently on the market.

SUMMARY OF THE INVENTION

It is an object of this invention to provide a package and method of packaging a bunch of flowers that preserves the freshness of the flower over a period of several days, much longer than when using the package and method of packaging according to the current art.

This invention is directed toward a flower sleeve comprising a tube of thin cellophane film that is closed on one end by a seal that extends across the end of the tube. Two parallel slits extend from the seal toward the open end. Each slit is generally about one to two inches long and is spaced about one inch from the other slit. A flap has one edge adhered to the inside of the sleeve between the end of the slits and the open end of the sleeve so that the flap generally lies against the inside of the sleeve. A pocket is formed by an additional film panel that is sealed to the outside of the sleeve. The pocket is open along a length of the edge of the pocket that is closest to the open end of the sleeve.

According to the method of practicing the invention, the bunch of flowers is stuffed into the sleeve through the open end of the sleeve such that the lower ends of the stems are adjacent to the sealed end of the sleeve.

Next, the nozzle end of a wand is inserted into the pocket. The other end of the wand communicates with a reservoir of nutrients in the form of a gel.

Gel is squirted from the nozzle of the wand through the slits and into the bottom end of the sleeve {tube). Once inside the sleeve, the gel is trapped thus allowing the cut flowers to receive the nutrients and maintain hydration.

Then a rubber band is wrapped around the sleeve at a location between the edge of the pocket and the open end of the sleeve thereby more or less forming an enclosure by the sleeve around the stem ends of the bunch of flowers. The gel is confined by the rubber band to the region of the sleeve where the lower ends of the stems are located. The flap over the slits acts as a "one way valve" that closes back over the slits and prevents gel that has been forced into the tube through the slits from flowing of seeping back out of the bag through the slits.

BRIEF DESCRIPTION OF THE FIGS.

FIG. 1 is a flow chart for making the sleeve.

FIG. 6 is a flow chart of the method for packaging a bouquet of flowers.

DESCRIPTION OF A BEST MODE

Turning now to a discussion of the drawings. FIG. 1 is a flow chart of the steps for making the flower sleeve of this invention.

Figure 2:
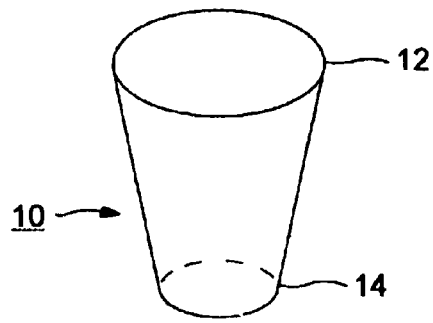
FIG. 2 shows a tube.

In step 1, a tube 10 of thin cellophane is made by any one of well-known methods. The tube is shown in FIG. 2 having two open ends, a large open end 12 and a small end 14 that is initially open but subsequently sealed.

In step 2, a second opening is formed in the tube.

Step 2 has several versions for providing a second opening in the tube for admitting a nutrient gel, depending on the circumstances of the application.

Figure 3:
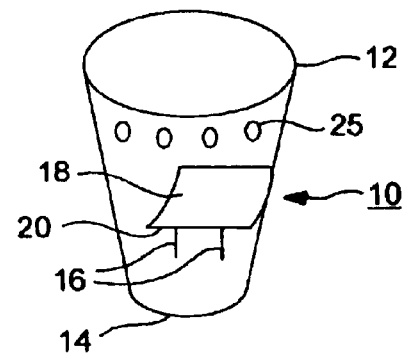
FIG. 3 shows one version of a flap.

In one version, as shown in FIG. 3, two slits 16 are cut extending from the small end 14 of the tube 10 toward the other end of the tube 12. The slits are typically about one and one half inches long.

An edge of a flap 18 is sealed inside the tube 10 along a line 20 perpendicular to the slits 16 and between the slits 16 and the open end 12 of the tube 10.

This can be accomplished by temporarily turning the tube 10 inside out partially so as to expose the inside surface of the tube 10 including the slits 16 and then heat sealing the edge of the flap 18 at the required location along line 20. The tube 10 is then returned to where the flap 18 is on the inside of the sleeve.

Figure 4:
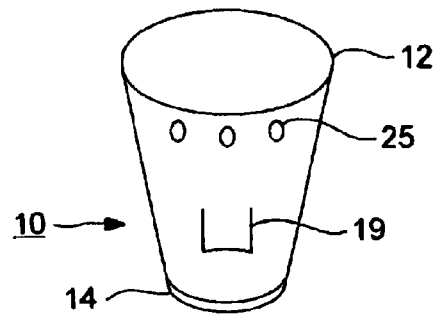
FIG. 4 shows another version of a flap.

Alternatively, as shown in FIG. 4, a substantially rectangular flap 19 is formed by cutting along three sides of a rectangular area leaving a flap 19 attached in the side of the tube.

In step 4, the lower end 14 of the tube 10 is sealed.

Figure 5:
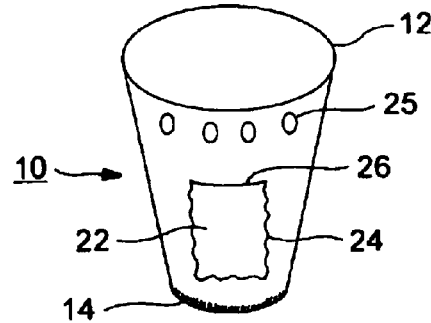
FIG. 5 shows a pocket on the side of the tube.

In step 5, as shown in FIG. 5, a pocket 22 is formed on the side of the tube over the area of the slits 16 (the slits 16 being the second opening, the open top of the tube being the first opening). The pocket is a panel 22 having a length of edge 24 sealed to the tube 10 except for an unsealed length of edge 26 that leaves an opening into the pocket 22 nearest the open end 12 of the tube 10.

The flap 16 performs like a one way valve. Gel that is inserted into the pocket under pressure forces the flap to "open" and admit gel into the region of the tube 10 adjacent to the sealed end 14 of the tube 10.

The version of FIG. 3 is more reliable as a seal than the version of FIG. 4 however both versions are embodiment of the invention.

The flower sleeve of this invention is now ready to receive the bouquet of flowers. The steps in the method for packaging the bouquet of flowers is listed in FIG. 6.

In step one, the bouquet is placed through the open end 12 of the tube 10 with cut ends of the bouquet closest to the sealed end 14 of the tube.

In step 2, the nozzle of a wand is inserted into the pocket 22. The wand communicates with a reservoir of nutrient gel.

In step 3, gel is squirted through the wand and through the slits 16 (the second opening in the tube 10) into the sealed end of the tube 10 whereby the stems become coated with the gel.

In step 4, a rubber band is wrapped around the tube so that the gel is confined to the lower end of the stems.

Variations and modifications of the method and flower sleeve of this invention may be contemplated after reading the specification and studying the figs. which are within the scope of the invention.

For example any one of several films may be used to form the flower sleeve including cellophane and polyethylene.

Openings other than slits shown in FIGS. 3 and 4 may be formed in the side of the tube 10.

The upper area of the tube 10 may have an array of apertures 25 to permit ethylene gas to escape from the bouquet. Cut flowers generate ethylene gas that can accelerate degradation of the bouquet if confined to the region occupied by the blossoms.

The flexible sheet comprising the tube is preferably about 0.005 inches thick. A practical range has a lower value of about 0.003 and an upper value 0.015 inches depending on the flower.

While the package described is especially suitable for packaging bouquets of flowers, the principles of the package of this invention is applicable to packaging other commodities as well. Other items could include bare roots, shrubs and small trees (e.g., the miniature "bonsai" trees).

Shipping small live trees having the root end of the trunk packaged in the sleeve of this invention with the roots coated with the gel may be preferable to having the roots encased in a bucket of sod. In this latter circumstance, the sod typically is watered by adding an excessive amount of water to the top surface of the sod in order to permeate the entire clump of sod.

The gel is selectable within a range of compounds depending on the item to be packaged. While gels having certain nutritious compositions suitable for flowers has been used to illustrate the invention, other application may require other gel compositions. For example, the gel may be an inert compound that excludes air from the item to be protected.

The gel may be perfumed to add to the attractiveness of the packaged bouquet.

In view of such variations and modifications, I therefore wish to define the scope of my invention by the appended claims.

I claim:

1. A package for packaging items which comprises:
    a container with a first opening arranged to permit inserting said items through said first opening into an interior of said package;
    said container having a second opening;
    a flap having an edge with a partial length of said edge adhered to an inside surface of said container arranged to provide that any force applied to said flap from inside said container forces said flap to close over said second opening;
    a pocket formed on an outside surface of said container over said second opening;
    said pocket having a pocket opening arranged to permit forcing a compound through said second opening from outside said container into said container wherein said compound is then prevented by said flap, closing over said second opening, from escaping from said container.

2. The package of claim 1 which further comprises a compound in said container in a vicinity of said second opening.

3. The package of claim 2 wherein said compound is a gel.

4. The package of claim 3 wherein said gel contains nutrients for cut flowers.

5. The package of claim 3 wherein said flap and said second opening comprises a substantially rectangular area of said tube having a slit along three edges of said area.

6. The package of claim 1 wherein said container comprises a flexible sheet.

7. The package of claim 6 wherein said second opening comprises a pair of slits in said container.

8. The package of claim 6 wherein said sheet is polyethylene.

9. The package of claim 6 wherein said sheet is cellophane.

10. The package of claim 6 wherein said sheet has a thickness of about 0.005 inches.

11. The package of claim 6 wherein said sheet has a thickness in a range of thicknesses from 0.003 inches to 0.015 inches.

12. The package of claim 6 wherein said item is a bouquet of flowers with stems and said first opening and said second opening are all operably arranged to permit positioning said bouquet in said container with said stems proximal to said second opening.

13. The package of claim 12 wherein said container has an array of openings adjacent said first opening arranged to provide ventilation to said bouquet.

14. The package of claim 13 wherein said container is a tube having one end sealed and another end being said first opening.

15. A flower sleeve for packaging a bouquet of flows comprising:
    a flexible plastic sheet formed into a tube having one end sealed and another end forming an opening through which a bouquet of flowers is positionable with stems of said bouquet proximal to said sealed end,
    a flap formed by a pair of slits formed in area of said tube extending from near said sealed end toward said open end and another slit connecting ends of said slit closest to said sealed end,
    a pocket formed by another plastic sheet over said area having a length of an edge adhered to an outside surface of said tube;
    said pocket having a pocket opening formed by leaving another length of said edge detached from said outside surface;
    said pocket, slits and flap arranged in operable combination to permit inserting said bouquet into said opening in said another end of said tube with stem ends of said bouquet adjacent to said sealed end of said tube permitting that a gel be forced into said pocket through said area into said tube after which said gel is prevented from escaping from said tube by said flap closing against an inside surface of said pocket.

16. A flower sleeve for packaging a bouquet of flows comprising:

a flexible plastic sheet formed into a tube having one end sealed and another end forming an opening through which a bouquet of flowers is insertable with stems of said bouquet proximal to said sealed ends, a pair of slits formed in an area of said tube extending from near said sealed end toward said open end, a flap having one edge sealed to an inside surface of said tube arranged such that, when a force is applied to said flap from inside said tube, said flap closes over said pair of slits;

a pocket formed by a portion of plastic sheet over said area having a length of an edge adhered to an outside surface of said tube;

said pocket having a pocket opening formed by leaving another length of said edge detached from said outside surface;

said pocket, slits and flap arranged in operable combination to permit inserting said bouquet into said opening in said another end of said tube with stem ends of said bouquet adjacent to said sealed end of said tube permitting that a gel be forced into said pocket through said area into said tube after which said gel is prevented from escaping from said tube by said flap closing against an inside surface of said pocket.

17. A package for packaging a bouquet of flowers which comprises:

A flexible tube with an opening on one end arranged to permit inserting said bouquet through said first opening into an interior of said package with stems of said bouquet oriented toward a sealed end of said tube;

said container having a second opening;

a flap having an edge with a partial length of said edge integral with an inside surface of said container arranged to provide that any force applied to said flap from inside said container forces said flap to close over said second opening;

a pocket formed on an outside surface of said container over said second opening;

said pocket having a pocket opening arranged to permit forcing a compound through said second opening from outside said container into said container wherein said compound is then prevented by said flap, closing over said second opening, from escaping from said container.

* * * * *